United States Patent [19]

Sangokoya

[11] Patent Number: 5,412,131
[45] Date of Patent: May 2, 1995

[54] TERITARY AMINO-ALUMINOXANE HALIDES

[75] Inventor: Samuel A. Sangokoya, Baton Rouge, La.

[73] Assignee: Albemarle Corporation, Richmond, Va.

[21] Appl. No.: 87,444

[22] Filed: Jul. 9, 1993

[51] Int. Cl.$^6$ .................................. C07F 5/06
[52] U.S. Cl. ............................. 556/175; 556/176; 556/179; 526/141; 526/154; 526/160; 502/117; 502/154
[58] Field of Search .................... 556/176, 179, 175

[56] References Cited

U.S. PATENT DOCUMENTS 5,329,032 7/1994 Tran et al. .................... 556/179

FOREIGN PATENT DOCUMENTS 0561476 9/1993 European Pat. Off. .
1319746 6/1973 United Kingdom .
366207 1/1973 U.S.S.R. .

OTHER PUBLICATIONS

Chem. Abstract, vol. 88, No. 6, #38222d, Meshkova, I. N., et al., "Alkylaluminoxanes as Cocatalysts of Ethylene Polymerization".
Chem. Abstract vol. 87, No. 14, #102851s, Chirkov, N. M., et al., "Catalyst for Polymerization of Olefins".
JACS (1968), pp. 3173–3177, "The Partial Hydrolysis of Ethylalane Compounds", by Alan Storr, et al.
JACS (1961), 83, pp. 542–546, "Aluminum–Nitrogen Polymers by Condensation Reactions", by A. W. Laubengayer, et al.
Journal of Organometallic Chemistry, (1980), 186, pp. 185–191, "Reactions of Tetraalkylaluminoxanes with Amines", by A. Piotrowski, et al.
Polyhedron, (1990) vol. 9, No. 2/3, pp. 429–453, "Alumoxanes:Synthesis, Structures, Complexes and Reactions", by S. Pasynkiewicz.

*Primary Examiner*—Romulo H. Delmendo
*Attorney, Agent, or Firm*—David M. Bunnell

[57] ABSTRACT

Novel tertiary amine-aluminoxane halide derivatives are disclosed along with olefin polymerization catalyst and polymerization processes using such derivatives in combination with metallocenes.

4 Claims, No Drawings

TERITARY AMINO-ALUMINOXANE HALIDES

This invention relates generally to soluble aluminoxane derivatives and more particularly to tertiary aminoaluminoxane halide derivatives, obtained by the reaction of aluminoxanes with less than stoichiometric amounts of tertiary amine hydrohalides, which in the presence of metallocenes form catalytically active compositions for olefin polymerization.

Pasynkiewicz (Polyhedron (1990), 9, 429–453) describes the synthesis and characterization of aluminoxane complexes with electron donor reagents. These reactions generally result in complex equilibrium products. Isolation of characterizable products from these reactions is often very difficult. Thus, a crystalline complex of tetramethylaluminoxane and N,N,N',N'-tetramethylethylenediamine (TMEDA) was obtained in 5–10% yield, by partial hydrolysis of trimethylaluminum (TMA) in TMEDA. Amines and ether complexes of aluminoxanes have been described, but they are usually unstable and decompose into the corresponding trialkylaluminum adduct, for example $Et_3Al \cdot THF$ and $Me_3Al \cdot PhOMe$. In almost all of the aluminoxane complexes, only the tetraalkylaluminoxane adducts, having one or two Al—O—Al bonds are formed. These materials are usually inactive or have inferior activity, compared to the regular oligomeric aluminoxanes, in olefin oligomerization or polymerization.

A British patent 1,319,746 describes the hydrolysis of $R_3Al$ ($C_2$ to $C_4$) in tertiary amine solvent whereby the resulting aluminoxane contained no amine (or N atoms) after removal of the amine by distillation.

Pasynkiewicz et. al. (Journal of Organometallic Chemistry (1980), 186, 185–191) also reported the preparation of complexes of tetraalkylaluminoxanes with benzylamine and methylamine. Although, these compounds are inactive in olefin polymerization, the authors showed by spectroscopic methods that the reaction products consisted of mixtures of different isomeric trimers.

Laubengayer et al. (J. Am. Chem. Soc., (1961), 83 542–546) have described the reactions of amines and amine hydrohalides with alkylaluminum compounds. Amines react with trialkylaluminum compounds to give different products. Thus, the reactions with tertiary, secondary and primary amines resulted in $R_3N \cdot AlR_3$ adducts, $[R_2N \cdot AlR_2]_2$ dimers and $[RN \cdot AlR]_n$ oligomers respectively. Similarly, amine hydrohalides react with alkylaluminum compounds to give different products. The reactions of $R_3N \cdot HX$ with $R_3Al$ and also that of $R_3N$ with $R_2AlX$ resulted in the same adduct product $R_3N \cdot AlR_2X$. Secondary amines, $R_2NH$, react with $R_2AlX$ just as $R_2NH \cdot HX$ reacts with $R_3Al$ to give the dimeric compound $[R_2N \cdot AlRX]_2$. However, the reactions of primary amines lead to formation of oligomeric products. Thus, $RNH_2$ reacts with $R_2AlX$ and $RNH_2 \cdot HX$ reacts with $R_3Al$ to give the oligomer $$[RNAlX]_n$$

where $n > 3$.

Storr et al. (J. Am. Chem. Soc., (1968), 90, 3173–3177) discloses the reaction of $(EtAlCl_2)O$ with excess trimethylamine to form a 1:1 complex $(EtAlCl)_2 \cdot NMe_3$.

The use of aluminoxanes in conjunction with metallocene compounds to oligomerize or polymerize olefin or olefinic compounds is well known. It is desirable to improve both the polymerization activity of the catalyst system and the quality of the polymer products. To this end, most research has exclusively focused on the modification of the metallocene compounds in order to effectuate the desired improvements. Examples of this endeavor are illustrated by U.S. Pat. Nos. 3,740,384, 4,945,076 and 5,034,549.

It is believed that the aluminoxane also has a major part to play in what happens during polymerization and it has now been discovered that the addition of an appropriate amount of a tertiary amine hydrohalide to the aluminoxane improves the solubility of the aluminoxane with a concomitant improvement in the activity of the catalyst system. For example, within the limits of the appropriate amount of added amine, a 20 to 80 percent increase in polymer yield compared to regular MAO is observed. However, when certain limits (>20%, amine:Al molar value) of addition is exceeded, a marked reduction in activity is observed.

In accordance with this invention there is provided a tertiary amino-aluminoxane halide derivative which comprises the reaction product of an aluminoxane and from about 0.005 to less than about 0.2 mole per mole of aluminum in said aluminoxane of a tertiary amine hydrohalide.

Also provided is an olefin polymerization catalyst comprising a metallocene and a tertiary amino-aluminoxane halide derivative which is the reaction product of an aluminoxane and from about 0.005 to less than about 0.2 mole per mole of aluminum in said aluminoxane of a tertiary amine halohalide.

Also provided is a process for polymerizing an olefin comprising contacting, under polymerization conditions, an olefin with a catalyst comprising a metallocene and a tertiary amino-aluminoxane halide derivative which is the reaction product of aluminoxane and from about 0.005 to less than about 0.2 mole per mole of aluminum in said aluminoxane of a tertiary amine hydrohalide.

Preferred aluminoxanes for use in making the tertiary amino-aluminoxane halide derivatives are hydrocarbylaluminoxanes.

Hydrocarbylaluminoxanes may exist in the form of linear or cyclic polymers with the simplest compounds being a tetraalkylaluminoxane such as tetramethylaluminoxane, $(CH_3)_2AlOAl(CH_3)_2$, or tetraethylaluminoxane, $(C_2H_5)_2AlOAl(C_2H_5)_2$. The compounds preferred for use in olefin polymerization catalysts usually contain about 4 to 20 of the repeating units:

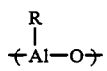

where R is $C_1$–$C_{10}$ alkyl and especially preferred are methylaluminoxanes (MAO). The methylaluminoxanes can contain some higher alkyl groups to improve their solubility. Such modified methylaluminoxanes are described, for example, in U.S. Pat. No. 5,157,008. Besides MAO, nonlimiting examples of hydrocarbylaluminoxanes for use in the invention include ethylaluminoxanes (EAO), isobutylaluminoxanes (IBAO), n-propylaluminoxanes, n-octylaluminoxanes, and the like.

The aluminoxanes can be prepared as known in the art by the partial hydrolysis of trialkylaluminum compounds. The trialkylaluminoxane compounds can be hydrolyzed by adding either free water or water containing solids, which can be either hydrates or porous materials which have absorbed water. Because it is difficult to control the reaction by adding water per se, even with vigorous agitation of the mixture, the free water is preferably added in the form of a solution or a dispersion in an organic solvent. Suitable hydrates include salt hydrates such as, for example, $CuSO_4.5H_2O$, $Al_2(SO_4)_3.18H_2O$, $FeSO_4.7H_2O$, $AlCl_3.6H_2O$, $Al(NO_3)_3.9H_2O$, $MgSO_4.7H_2O$, $ZnSO_4.7H_2O$, $Na_2SO_4.10H_2O$, $Na_3PO_4.12H_2O$, $LiBr.2H_2O$, $LiCil.1H_2O$, $LiI.2H_2O$, $LiI.3H_2O$, $KF.2H_2O$, $NaBr.2H_2O$ and the like and alkali or alkaline earth metal hydroxides such as, for example, $NaOH.H_2O$, $NaOH.2H_2O$, $Ba(OH)_2.8H_2O$, $KOH.2H_2O$, $CsOH.1H_2O$, $LiOH.1H_2O$ and the like. Mixtures of any of the above hydrates can be used. The mole ratios of free water or water in the hydrate or in porous materials such as alumina or silica to total alkyl aluminum compounds in the mixture can vary widely, such as for example from about 2:1 to 1:4 with ratios of from about 4:3 to 1:3.5 being preferred.

Such processes for preparing hydrocarbylaluminoxanes are described, for example, in U.S. Pat. No. 4,908,463. The methylaluminoxanes contain varying amounts, of from about 5 to 35 mole percent, of the aluminum value as unreacted trimethylaluminum.

The tertiary amine hydrohalides for use in the invention can be represented by the formula $R_3N.HX$ where each R is selected from $C_1$ to $C_{20}$ cyclic or linear hydrocarbyl groups and X is any halogen and, preferably, Cl. Non-limiting examples of tertiary amine hydrohalides include aliphatic or aromatic tertiary amine hydrohalides such as, trimethylamine hydrochloride, trimethylamine hydrobromide, trimethylamine hydrofluoride, triethylamine hydrochloride, triethylamine hydrobromide, triethylamine hydrofluoride, tribenzylamine hydrochloride, tribenzylamine hydrobromide, tribenzylamine hydrofluoride, and the like.

The tertiary amino-aluminoxane hydrohalide can be prepared by reacting the aluminoxane and tertiary amine hydrohalide in an organic solvent in molar proportions of amine hydrohalide (N or X) of from about 0,005 to less than about 0.2 mole per mole of aluminum in the aluminoxane and preferably from about 0.01 to 0.15 mole of amine hydrochloride per mole of aluminum. Amounts of 0.2 mole per mole have reduced polymerization activity compared with untreated aluminoxane. Mixtures of aluminoxanes and tertiary amine hydrohalides can be used in forming the derivatives. Any inert organic solvent can be used as the reaction medium. Non-limiting examples of solvents include aliphatic hydrocarbons such as pentane, isopentane, hexane, cyclohexane, heptane, octane, decane, dodecane, hexadecane, octadecane and the like with those having carbon numbers of 5 to 10 being preferred and aromatic hydrocarbons such as benzene, toluene, xylene, cumene and the like with those having carbon numbers of 6 to 20 being preferred. Generally amounts of solvent to provide a total concentration of reactants of from about 10 to 30 wt. percent are used.

Preferred reaction temperatures range from about 25° to 90° C.

The tertiary amino-aluminoxane derivatives can be used in combination with metallocenes to provide olefin polymerization catalysts. Such metallocenes are well known in the art and non-limiting examples include the metallocenes of Groups 3, 4, 5, 6, lathanide and actinide metals such as the metallocenes of transition metals which are described in published European patent application No. 0 129,368 and U.S. Pat. Nos. 5,017,714, 5,026,798 and 5,036,034, whose teachings with respect to such metallocenes are incorporated herein by reference. Illustrative examples of such metallocenes are bis-(cyclopentadienyl)zirconium dimethyl, bis-(cyclopentadienyl)zirconium dichloride, bis-(cyclopentadienyl)zirconium monomethylmonochloride, bis-(cyclopentadienyl)titanium dichloride, bis-(cyclopentadienyl)titanium difluoride, cyclopentadienylzirconium tri-(2-ethylhexanoate), bis-cyclopentadienyl)-zirconium hydrogen chloride, bis-(cyclopentadienyl)-hafnium dichloride and the like.

The catalyst components are used in proportions to provide mole ratios of metal atom in the metallocene to aluminum atom in the amino-aluminoxane of from about 0.0002:1 to 0.2:1 and preferably 0.0005:1 to 0.02:1. The catalyst components can be used in solution or deposited on a solid support. The solid support can be any particulate solid, and particularly porous supports such as talc or inorganic oxides, or resinous support material such as polyolefins. Preferably, the support material is an inorganic oxide in finely divided form.

Suitable inorganic oxide support materials which are desirably employed include Group IIA, IIIA, IVA or IVB metal oxides such as silica, alumina, silica-alumina and mixtures thereof. Other inorganic oxides that may be employed either alone or in combination with the silica, alumina or silica-alumina are magnesia, titania, zirconia, and the like. Other suitable support materials are finely divided polyolefins such as finely divided polyethylene.

The catalysts are effective to produce olefin polymers and especially ethylene polymers and ethylene/α-olefin copolymers. Examples of olefins that can be polymerized in the presence of the catalysts of the invention include α-olefins having 2 to 20 carbon atoms such as ethylene, propylene, 1-butene, 1-hexene, 4-methyl-1-pentene, 1-octene, 1-decene, 1-dodecene, 1-tetradecene, 1-hexadecene, and 1-octadecene. Polymerization of ethylene or copolymerization with ethylene and an α-olefin having 3 to 10 carbon atoms is preferable. Such polymerizations may be performed in either the gas or liquid phase (e.g. in a solvent, such as toluene, or in a diluent, such as heptane). The polymerization can be conducted at conventional temperatures (e.g., 0° to 120° C.) and pressures (e.g., ambient to 50 $kg/cm^2$) using conventional procedures as to molecular weight regulations and the like.

The invention is further illustrated by, but is not intended to be limited to, the following examples.

The following examples were carried out under inert atmosphere conditions, using Schlenk glassware and vacuum line, in conjunction with a $N_2$-drybox. Solvents were distilled using standard methods. Filtration and vacuum distillation were done inside a $N_2$-drybox and distillates were collected in a trap at −78° C. Solid tertiary amine hydrohalides were used without further purification except drying. Aluminoxanes were obtained from stock solutions produced by Ethyl Corporation.

EXAMPLE 1

A 10 wt. % toluene solution of methylaluminoxane (MAO, 260 mmol Al) was placed in a reaction flask in a $N_2$-dry box. Trimethylamine hydrochloride (0.25 g, 2.6 mmol) was added in batches. Gas evolution (methane) was observed. After the addition was completed, the mixture was stirred at room temperature for about 30 minutes. Dissolved gas was allowed to escape. The reaction flask was then heated (oil bath) at about 70° C. for about one hour. The initially cloudy MAO solution became clearer.

The product solution was filtered with some difficulties through a medium frit. After filtration, the solution remained clear even after four months. The final product contained 218 mmol of Al, which is 84% of the initial aluminum value. Some of the liquid product was concentrated under vacuum to give a free flowing, colorless solid product. Analyses of the liquid and solid products are shown in Table 1. The product is found to be more active than regular MAO for ethylene polymerization (Table 2).

EXAMPLE 2

A 30 wt. % MAO solution in toluene (300 mmol Al) was allowed to react with trimethylamine hydrochloride (15 mmol) as described in Example 1. After addition of the amine compound, the cloudy MAO solution immediately turned clear. The mixture was stirred at room temperature overnight. Filtration through a medium frit was a lot easier than in Example 1. The recovered aluminum value was almost quantitative (>99%). A free flowing, solid product was also obtained by concentration via vacuum. Increased activity was observed in the ethylene polymerization test. (Table 2)

COMPARISON 1

To a 30 wt. % solution of MAO in toluene (30 g, 104.4 mmol Al) Me$_3$NHCl (2.0 g, 20.9 mmol) was added in batches. Gas evolution was observed. The mixture was stirred overnight at room temperature to give a clear solution. Filtration through a medium frit was very easy. A solid MAO product was obtained after removing all solvents by vacuum distillation. Product analysis is shown in Table 1. This product was found to be inactive in ethylene polymerization. (Table 2)

EXAMPLE 3

A 10 wt. % toluene solution of MAO (125 g, 275 mmol Al) was allowed to react with triethylamine hydrochloride (0.76 g, 5.5 mmol). After addition and gas evolution, the mixture was heated at 70° C. (oil bath) during a period of one hour. Filtration was easier than in Example 1. A portion of the liquid product was concentrated to dryness in order to obtain solid MAO product. Analyses of the products are shown in Table 1. This product was found to be active in ethylene polymerization. (Table 2)

EXAMPLE 4

MAO (54 g, 108 mmol Al) was treated with triethylamine hydrochloride (1.1 g, 8.1 mmol) as described in Example 1. The resulting clear solution which remained clear, even after four months, was found to be active in ethylene polymerization. A portion of the product was evaporated to dryness. No TMA was detected in the solid product by pyridine titration.

COMPARISON 2

Et$_3$NHCl (9.4 g, 68 mmol) was added in batches during a period of about 90 minutes to a MAO solution (340 mmol Al). After addition, the mixture was allowed to stir at room temperature overnight. A lot of gas evolution was observed. The mixture was heated at 90° C. (oil bath) for about two hours. Filtration through a medium frit was fast and easy. An attempt to obtain solid product by concentration to dryness resulted in an oily, low melting solid. Furthermore, an attempt to use this product as a co-catalyst in ethylene polymerization resulted in a negligible production of polyethylene. Polyethylene productivity was somewhat improved by addition of TMA (Table 2).

EXAMPLE 5

MAO (110 g, 187 mmol al) was allowed to react with triethylamine hydrofluoride (1.13 g, 9.35 mmol) as described in Example 1. A little by-product in the form of a liquid clathrate was observed. This was removed via a separatory funnel. The calathrate formation presumably occurred due to some Et$_4$NF impurities in the Et$_3$N.HF. However, the major product, triethylaminoaluminoxane fluoride, was found to be very active in ethylene polymerization.

TABLE 1

Tertiary Amine Hydrohalide Treated MAO Product Analysis

| Example | Amine/Al Mole Ratio | Soluble Aluminum Recovered (%) | Al/Cl Mole Ratio | Methane/Al Ratio | TMA$^a$ Content (%) |
| --- | --- | --- | --- | --- | --- |
| 1 (L) | .01 | 84 | 96 | 1.5 | 20 |
| 1 (S) | .01 | — | 85 | 1.2 | ND$^b$ |
| 2 (L) | .05 | 99 | 21.8 | 1.55 | 21 |
| 2 (S) | .05 | — | 17.2 | 1.3 | ND |
| Comparison 1 (L) | .20 | 99 | 5.3 | 1.39 | 7.6 |
| Comparison 1 (S) | .20 | — | 4.8 | 1.3 | ND |
| 3 (L) | .02 | 90 | 47 | 1.45 | 18 |
| 3 (S) | .02 | — | 45 | 1.15 | ND |
| 4 (L) | .075 | 77 | 19.6 | 1.44 | 23 |
| 4 (S) | .075 | — | 19.8 | 1.36 | ND |
| Comparison 2 (L) | .20 | 95 | 4.94 | 1.32 | 3.4 |
| Comparison 2 (S) | .20 | — | 4.02 | 1.2 | ND | a Determined by pyridine titration
b Not detectable
L = liquid product
S = solid product

EXAMPLE 6

Polymerization of Ethylene

Liquid and solid products from the above mentioned Examples were used in conjunction with zirconocene dichloride to polymerize ethylene.

Inside a N$_2$-dry box, an autoclave (600 mL) was changed with toluene (250 mL). A mixture of the tertiary amine hydrohalide treated MAO product (10 mmol Al) and zirconocene dichloride (6.8×10$^{-6}$ mol) in toluene (50 ml) was added. Then the autoclave was brought out and set up in a hood. The reactor was heated to 80° C. and then ethylene was introduced at 60 psi during 10 minutes. The reaction was quenched by addition of methanol (300 mL). The polyethylene produced was initially air dried, followed by drying in a vacuum oven without heating. Yield of polyethylene and activity of the catalyst compositions are reported in Table 2.

TABLE 2

Ethylene Polymerization Test[a] Tertiary Amine Hydrohalide Treated MAO

| MAO Composition (10 mmol Al) | Zirconocene Dichloride (moles × $10^{-6}$) | Al/Zr mole ratio | Activity (× $10^6$) g(PE)/mol. Zr · atm · hr | Activity Compared to Regular MAO | PE (g) |
|---|---|---|---|---|---|
| Example 1 (L) | 6.8 | 1470 | 9.52 | 1.69 | 44 |
| Example 2 (S) | 6.8 | 1470 | 9.08 | 1.62 | 42 |
| Comparison 1 (L) | 6.8 | 1470 | — | — | 0 |
| Example 3 (L) | 6.8 | 1470 | 9.30 | 1.65 | 43 |
| Example 3 (S) | 6.8 | 1470 | 9.08 | 1.62 | 42 |
| Example 4 (L) | 6.8 | 1470 | 10.60 | 1.89 | 49 |
| Comparison 2 (L) | 6.8 | 1470 | — | — | 0 |
| Comparison 2 (L) plus TMA[b] | 6.8 | 1470 | 2.59 | 0.46 | 12 |
| Regular[c] MAO | 6.8 | 1470 | 5.62 | 1 | 26 |

[a]Conducted at 60 psi ethylene, 90° C., in toluene (300 ml) for 10 minutes.
[b]TMA addition, 8 mmol Al in MAO, 2 mmol Al in TMA
[c]Control experiment using untreated MAO solution.

The results shown in Table 2 illustrate that amounts of 0.2 moles of amine per mole of aluminum gave reduced activity compared to untreated MAO whereas amounts of from 0.01 to 0.075 gave activities of up to almost twice that of untreated MAO (Example 4).

What is claimed is:

1. A tertiary amino-aluminoxane halide composition comprising the reaction product obtained by reacting an aluminoxane and from about 0.005 to less than about 0.15 mole per mole of aluminum in said aluminoxane of a tertiary amine hydrohalide in an inert organic solvent at a temperature of from about 25°-to 90° C.

2. The composition of claim 1 wherein from about 0.01 to about 0.075 mole of tertiary amine hydrohalide per mole of aluminum in said aluminoxane is present.

3. The composition of claim 1 wherein the tertiary amine hydrohalide is a hydrochloride or a hydrofluoride and the aluminoxane is a methylaluminoxane.

4. The composition of claim 3 wherein the tertiary amine hydrohalide is selected from the group consisting of trimethylamine hydrochloride, triethylamine hydrochloride, trimethylamine hydrofluoride and triethylamine hydrofluoride.

* * * * *